United States Patent [19]

Cosentino et al.

[11] Patent Number: 5,508,046
[45] Date of Patent: Apr. 16, 1996

[54] STABLE, ANTICORROSIVE PERACETIC/PEROXIDE STERILANT

[75] Inventors: Louis C. Cosentino, Deephaven, Minn.; Walter B. Jansen, Sandy, Utah; Robert T. Hall, II, Welch, Minn.; Rosario M. Marino, Bogota, Colombia; Kimberly L. Hall, Welch, Minn.

[73] Assignee: Minntech Corporation, Minneapolis, Minn.

[21] Appl. No.: 162,065

[22] PCT Filed: Jul. 14, 1992

[86] PCT No.: PCT/US92/05877

§ 371 Date: Dec. 9, 1993

§ 102(e) Date: Dec. 9, 1993

[87] PCT Pub. No.: WO93/01822

PCT Pub. Date: Feb. 4, 1993

[51] Int. Cl.$^6$ ............................ A61K 33/40; A61K 33/32; A61K 33/26
[52] U.S. Cl. .................... 424/616; 424/639; 424/646; 514/557
[58] Field of Search ..................... 424/616, 639, 424/646; 514/557

[56] References Cited

U.S. PATENT DOCUMENTS

| | | | |
|---|---|---|---|
| 4,051,058 | 9/1977 | Böwing et al. | 252/186 |
| 4,051,059 | 9/1977 | Böwing et al. | 252/186 |
| 4,557,898 | 12/1985 | Greene et al. | 422/28 |
| 4,587,264 | 5/1986 | Jourdan-Laforte | 514/557 |
| 4,743,447 | 5/1988 | LaRouzic et al. | 424/130 |
| 4,812,173 | 3/1989 | Tsao et al. | 134/27 |
| 4,963,157 | 10/1990 | Machida et al. | 8/111 |
| 4,971,782 | 11/1990 | Rudy et al. | 424/53 |
| 5,008,106 | 4/1991 | Merianos et al. | 424/80 |

FOREIGN PATENT DOCUMENTS

| | | |
|---|---|---|
| 0147207 | 7/1985 | European Pat. Off. . |
| 8701147 | 5/1987 | WIPO . |
| 9001862 | 4/1990 | WIPO . |

OTHER PUBLICATIONS

Chemical Abstracts 114:30209 (1989). Remy et al.
Seymour S. Block, Ph. D., "Peroxygen Compounds," *Disinfection, Sterilization and Preservation*, 4th Ed., Lea & Febiger, 9:167–181 (1991).
U.S. Food & Drug Admin., "Indirect Food additives:adjuvants, production aids, and sanitizers: hydrogen peroxide, etc.," *Chemical Abstracts*, vol. 104, No. 19; May 12, 1986, p. 547, Col. 2.
English Abstract of Fed. Rep. of Germany Publication No.: 3134050 A1 Publication Date: Mar. 10, 1983.
English Translation of EP: 89403013.9 (0370850 A1) Publication Date: May 30, 1990.

Primary Examiner—Zohreh Fay
Attorney, Agent, or Firm—Barbara A. Wrigley; Amelia A. Buharin

[57] ABSTRACT

Stable microbicides comprising hydrogen peroxide, peracetic acid, acetic acid and purified water substantially free of contaminants, sequestrants or stabilizers and having anticorrosive properties for metals used in surgical and dental instruments is disclosed.

12 Claims, 7 Drawing Sheets

STABLE, ANTICORROSIVE PERACETIC/PEROXIDE STERILANT

BACKGROUND OF THE INVENTION

1. Field of the Invention

This invention relates generally to the field of microbicides. In particular, it relates to a stable microbicide having anticorrosive properties comprising a mixture of hydrogen peroxide, peracetic acid, acetic acid and purified water which is substantially free of contaminants or stabilizing and sequestrant type additives.

2. Description of the Related Art

Peracetic acid/peroxide containing compositions have a long history of use as disinfectants and sterilizers due to their microbicidal activities. However, peroxide containing compositions are high-energy-state compounds and as such can be considered thermodynamically unstable. Therefore, because there is a strong tendency for these compositions to decompose in the presence of multivalent metal ions, stabilizers are added. Stabilizers may be agents such as sodium pyrophosphate, phosphonic acid or chelating agents such as 8-hydroxyquinoline. Stabilizers act by removing trace metals which accelerate the decomposition of peroxides. Stabilizers also accelerate the reaction between hydrogen peroxide and acetic acid to form peracetic acid. Therefore, for any given concentration of hydrogen proxide and acetic acid, the addition of a stabilizer increases the concentration at equilibrium of peracetic acid.

While conventional art compositions are stable due to the use of added stabilizers, they are also highly corrosive to the very metals they are designed to disinfect namely surgical and dental instruments made of aluminum or brass, which instruments are often plated with an ornamental or protective layer of nickel or nickel and/or chromium. Additionally, certain susceptible individuals often exhibit allergic reactions to the conventional art formulations. Further, after prolonged use these conventional art formulations often leave mineral-like deposits on the metal instruments they sterilize.

A concentrated composition that contains no stabilizer or sequestrant type additives that is both stable during storage for prolonged periods of time and possesses anticorrosive properties would be a decided advantage over these conventional formulations. Further, a use-dilution formulation that may be reused several times, is stable for relatively long periods in the diluted form and possesses anticorrosive properties would be a further advantage over conventional formulations.

SUMMARY OF THE INVENTION

It is an object of the stable, anticorrosive concentrate and use-dilution microbicides in accordance with the present invention to solve the problems outlined above that has heretofore inhibited long-term storage and the anticorrosive sterilization of surgical and dental instruments. These improved microbicide solutions not only have the desired stability but have been shown to have a significantly reduced corrosive effect on certain metals than those of conventional art mixtures of the peracetic acid/peroxide types known to the applicants.

In accomplishing the foregoing objectives, there has been provided in accordance with the present invention a stable, anticorrosive to surgical and dental metals concentrate including peracetic acid, acetic acid, hydrogen peroxide and purified water mixed in a ratio of from about one to eleven parts total acid to one part hydrogen peroxide. The new concentrate has from substantially about 0.001 ppm to 200 pm, more preferably from about 0.001 ppm to 100 ppm, and most preferably from about 0.001 ppm to 10 ppm of added stabilizers, such as phosphonic acids, sodium pyrophosphates and from about 0.001–10 ppm of ionic and non-ionic contaminants such as divalent and trivalent ions, with no added surfactants, such as ethoxylated decyl alcohols, sulfonate and sulfate types.

In accordance with another aspect of the present invention, there has been provided a stable, anticorrosive to surgical and dental metals use-dilution formulation including a concentrate consisting essentially of at equilibrium peracetic acid, acetic acid, hydrogen peroxide and an aqueous diluent, said concentrate characterized in having from about 0.001–200 ppm of added stabilizers, from about 0.001–10 ppm of ionic and nonionic contaminants and no added surfactants; and a purified aqueous diluent; wherein the concentrate is diluted in the aqueous diluent from about 20 to 40 times.

In accordance with still another aspect of the present invention, there has been provided a process for preparing a sterilant concentrate as described above, including the steps of introducing from about 17% by weight to about 40% by weight hydrogen peroxide into a mixing drum, the hydrogen peroxide having from about 0.001–200 ppm of added stabilizers; blending thereinto from about 10% by weight to about 16% by weight acetic acid; and adding a purified aqueous diluent having from about 0.001–10 ppm of divalent and trivalent ions; wherein the equilibrium concentration includes from about 16–38% by weight hydrogen peroxide; from about 2.5–9% by weight acetic acid; from about 1.5–6.0% by weight peracetic acid; and an aqueous diluent and wherein the equilibrium concentration is characterized in having from about 0.001–200 ppm of added stabilizers, from about 0.001–10 ppm of ionic and nonionic contaminants and no added surfactants.

One of the advantages of the present invention is that the occasional allergic reactions of some individuals to the conventional art formulations is reduced. Another advantage of the present invention is that the presence of mineral-like deposits from the use of the solutions of conventional art formulations containing sequestrants or stabilizers is no longer found. Perhaps most importantly, however, the present invention allows metal instruments such as dental tools and surgical instruments to be sterilized with significantly reduced corrosivity as will be shown.

Further objects, features and advantages of the present invention will become apparent from the detailed description of the preferred embodiments, including the best mode, which follow.

DETAILED DESCRIPTION OF THE INVENTION

Concentrate microbicide formulations in accordance with the present invention possess the desirable property of a long storage life without deleterious decomposition despite the absence of conventional additions of stabilizers and sequestrants as heretofore taught in the art. Additionally, the concentrate compositions of the present invention are far less corrosive to metals that are sterilized using the compositions such as surgical and dental instruments. In contrast with conventional art formulations containing added surfactants, sequestrants and other stabilizers where visible evidence of corrosion of the metals appeared in one or two hours, formulations in accordance with the preferred embodiment of the present invention visibly showed comparatively little corrosion on the same metals during the same time period.

Manufacture of the preferred embodiment is effected by mixing a solution of hydrogen peroxide with acetic acid diluted with a purified aqueous diluent. The hydrogen peroxide is selected from commercially available sources having low concentrations of stabilizers, preferably 0.001 ppm to 200 ppm, more preferably from about 0.001 ppm to 100 ppm, and most preferably from about 0.001 ppm to 15 ppm of added stabilizers, such as phosphonic acids, sodium pyrophosphates. Sources of such hydrogen peroxide are available from FMC Corporation (Philadelphia, Pa.).

In addition, the preferred embodiment in accordance with the present invention preferably includes no contaminants. Contaminants such as divalent and trivalent ions, principally, iron, manganese, magnesium, nickel and cobalt, and undesirable trace organics found in the manufacturing process, principally, surfactants, acetone, methanol, ethanol, which are typically present in conventional art formulations are found in the present invention in amounts preferably from about 5–10 ppm and most preferably from about 0.001–5 ppm in the final composition.

Referring to Table I, the preferred composition is shown.

TABLE I

|  | Initial Mixture | After Equilibrium |
|---|---|---|
| $H_2O_2$ | 17–40% by wt. | 16–38% by wt. |
| HOAc | 10-16% by wt. | 2.5–9.0% by wt. |
| HOOAc | 0 | 1.5–6.0% by wt. |

The concentrate microbicide in accordance with the present invention may be formulated over a wide range of concentrations of the active materials. After equilibrium the concentrate microbicide may have as high as 38% by weight hydrogen peroxide at equilibrium with the peracetic acid concentration ranging from 1.5% to 6.0% as indicated in Table 1. Since the concentrate when initially mixed contains no peracetic acid and therefore is not used immediately, it is stored for approximately 19–20 days until the solution equilibrates and peracetic acid is formed by the reaction of hydrogen peroxide with acetic acid as illustrated in Reaction 1.

REACTION 1

$$CH_3CO_2H + H_2O_2 \rightarrow CH_3CO_3H + H_2O$$

Figure 1:
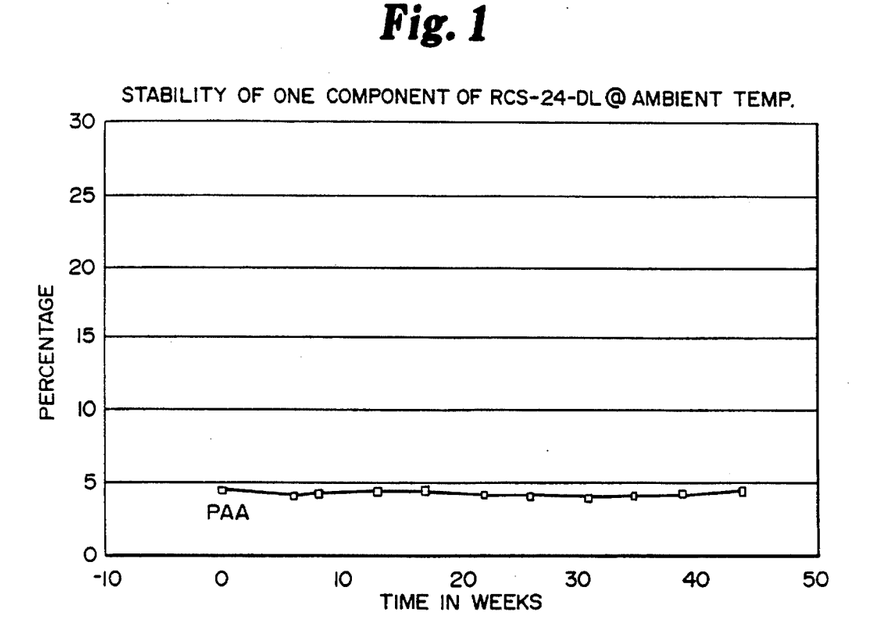
FIG. 1 is a chart of stability of the concentrated microbicide against time where the initial formulation contained 4.1% by weight of peracetic acid and the storage temperature was at ambient temperature of 22° C.
Figure 2:
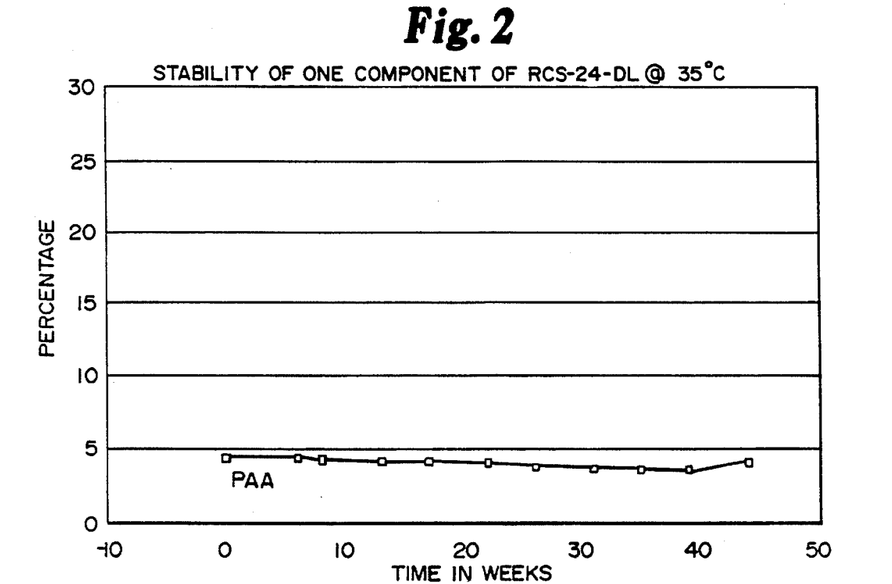
FIG. 2 is a chart of stability of concentrated microbicide where the initial formulation contained 4.5% by weight of peracetic acid and the storage temperature was 35° C.
Figure 3:
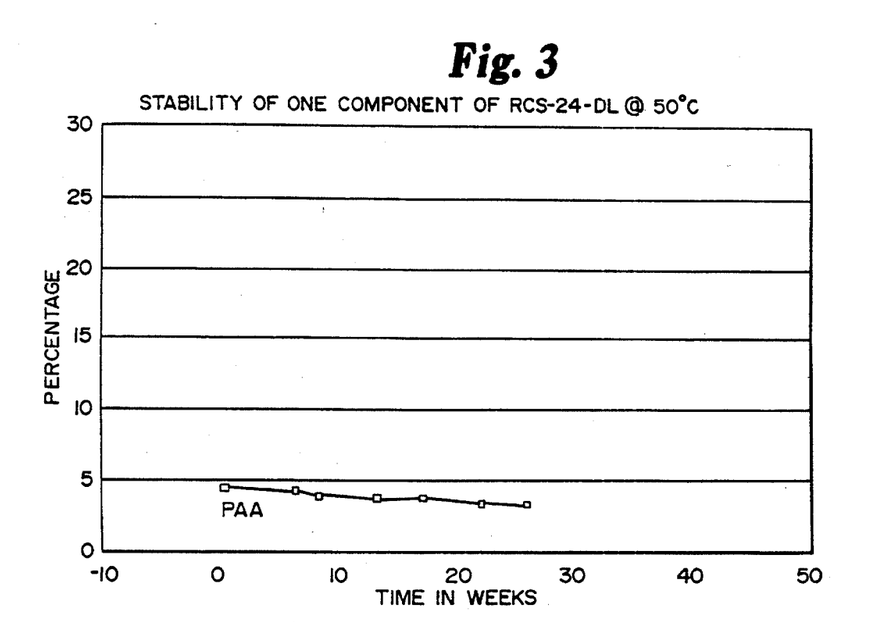
FIG. 3 is a chart of stability of the concentrated microbicide against time where the initial formulation contained 4.2% by weight of peracetic acid and the storage temperature was 50° C.
Figure 4:
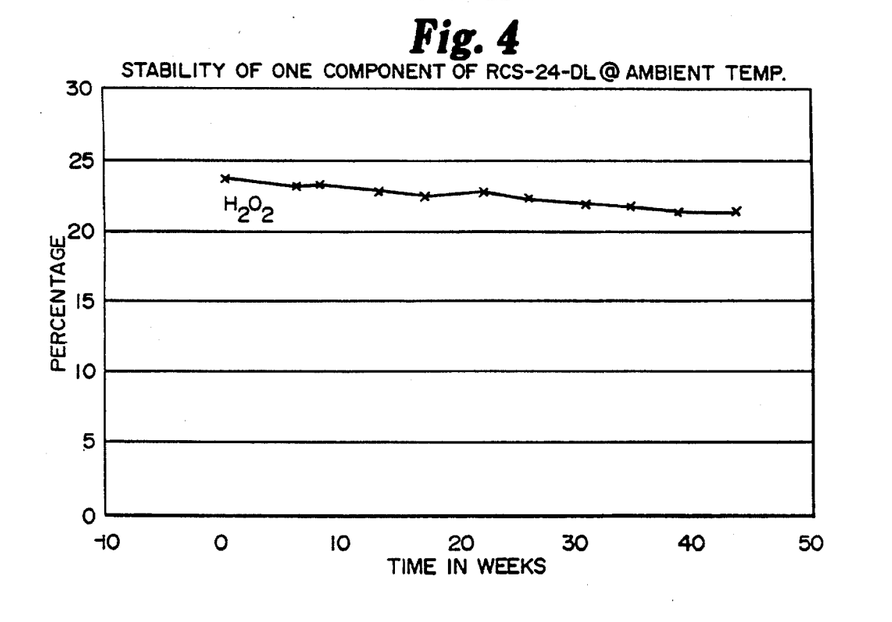
FIG. 4 is a chart of stability of the concentrated microbicide against time where the initial formulation contained 23% by weight of hydrogen peroxide and the storage temperature was 22° C.
Figure 5:
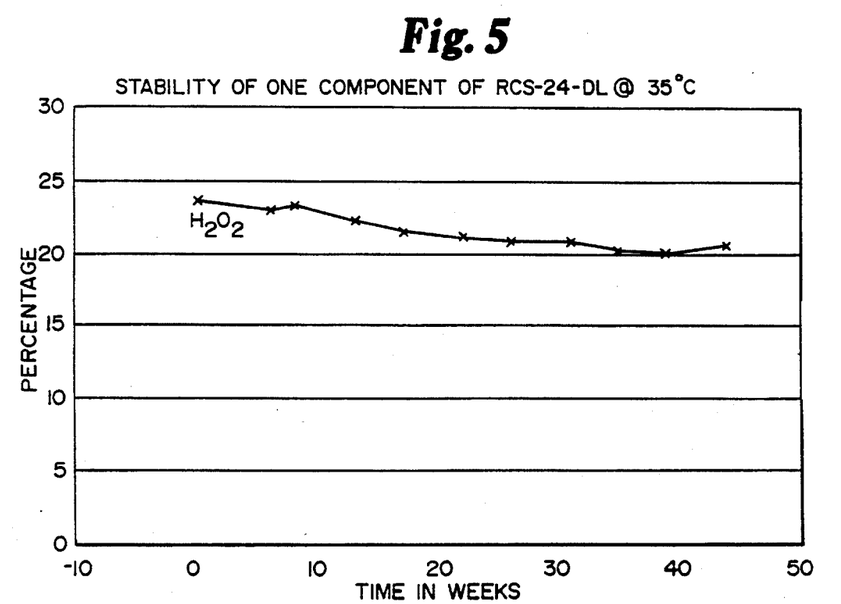
FIG. 5 is a chart of stability of the concentrated microbicide against time where the initial formulation contained 23% by weight of hydrogen peroxide and the storage temperature was 35° C.
Figure 6:
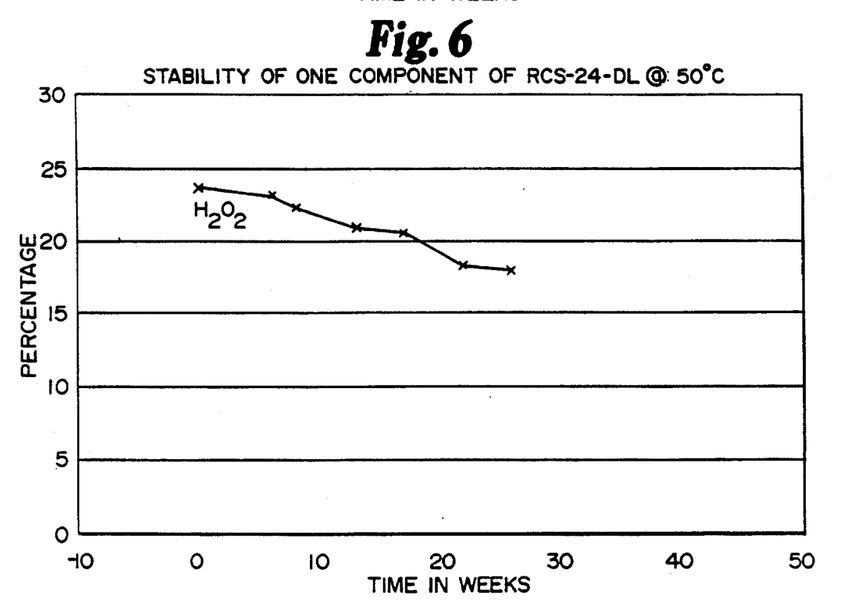
FIG. 6 is a chart of stability of the concentrated microbicide against time where the initial formulation contained 23% by weight of hydrogen peroxide and the storage temperature was 50° C.
Figure 7:
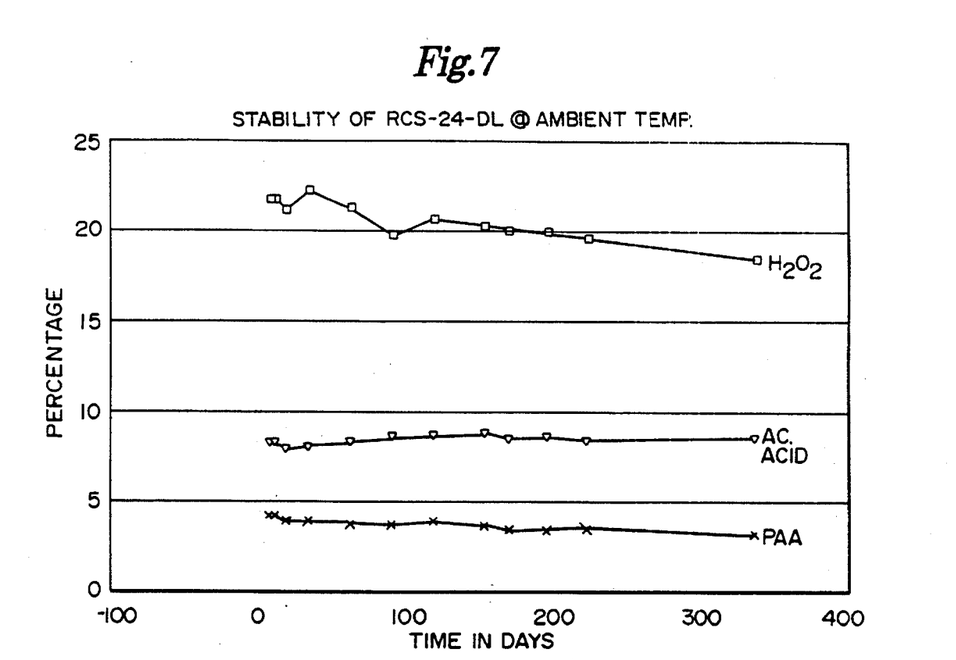
FIG. 7 is a chart of stability of the concentrated microbicide against time where the initial formulation contained 23% by weight of hydrogen peroxide, 4% by weight of peracetic acid and 8.4% acetic acid and the solution was stored at ambient temperature.
Figure 8:
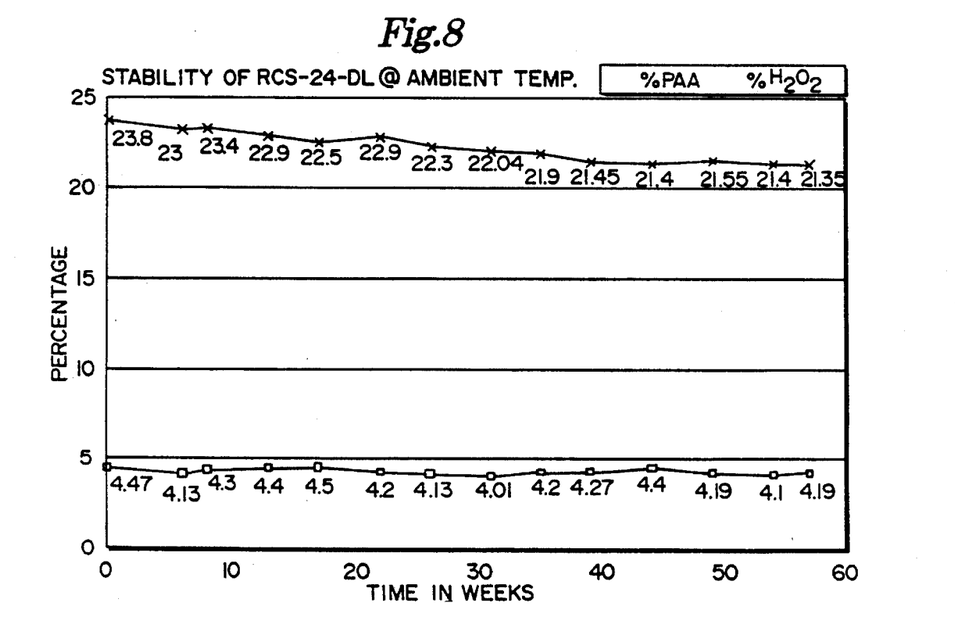
FIG. 8 is a chart of stability of the concentrated microbicide against time where the initial formulation contained 23.8% by weight hydrogen peroxide and 4.47% by weight peracetic acid and the solution was stored at ambient temperature.
Figure 9:
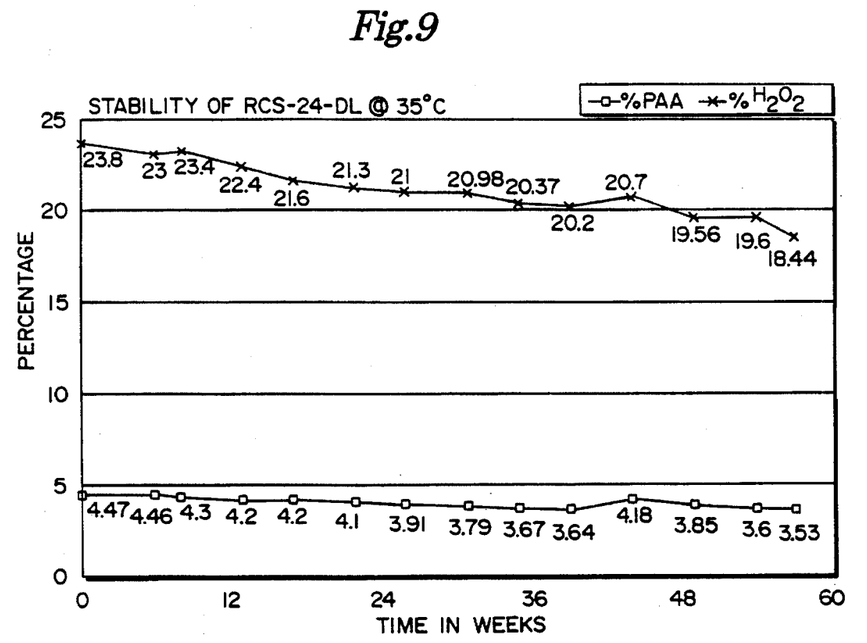
FIG. 9 is a chart of stability of the concentrated microbicide against time where the initial formulation contained 23.8% by weight hydrogen peroxide and 4.47% peracetic acid and the storage temperature was 35° C.
Figure 10:
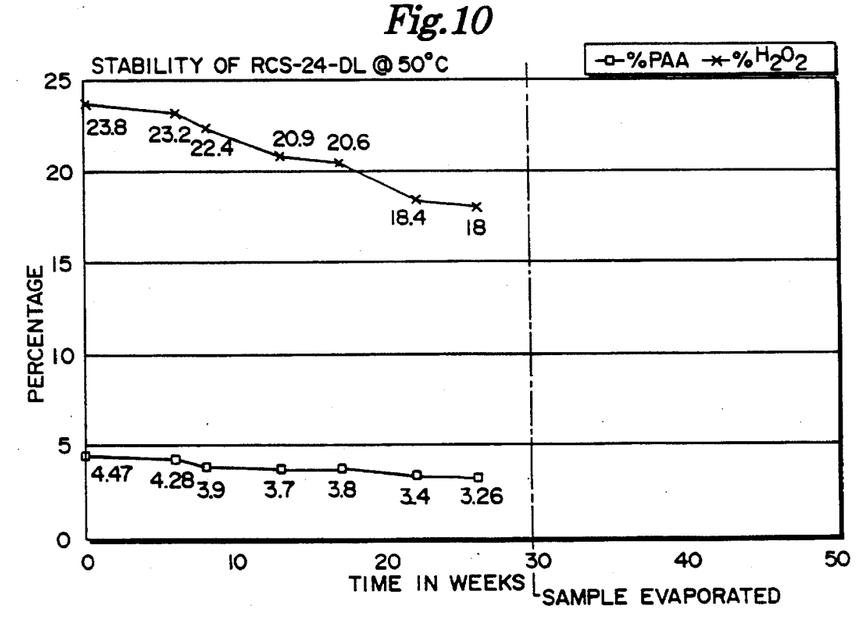
FIG. 10 is a chart of stability of the concentrated microbicide where the initial formulation contained 23.8% by weight hydrogen peroxide and 4.47% by weight peracetic acid and the storage temperature was 50° C.
Figure 11:
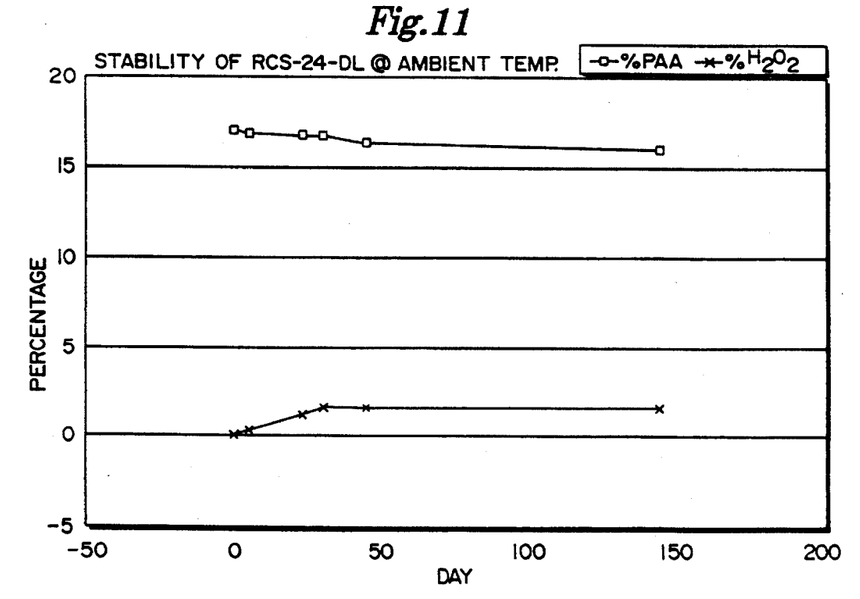
FIG. 11 is a chart of stability of the concentrated microbicide where the initial formulation contained 17.2% by weight hydrogen peroxide and 0.0% by weight peracetic acid and the solution was stored at ambient temperature.
Figure 12:
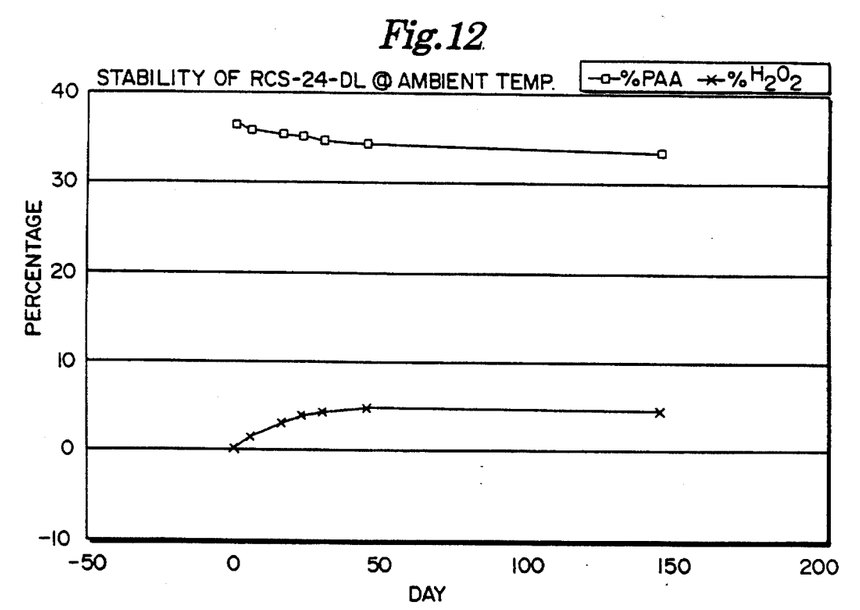
FIG. 12 is a chart of stability of the concentrated microbicide where the initial formulation contained 36.46% by weight hydrogen peroxide and 0.0% by weight peracetic acid and the solution was stored at ambient temperature.
Figure 13:
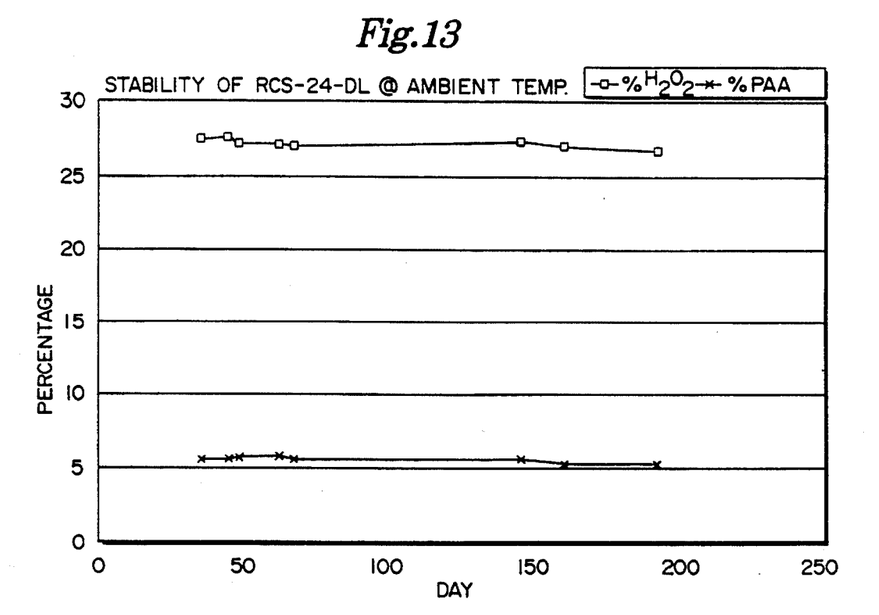
FIG. 13 is a chart of stability of the concentrated microbicide where the initial formulation contained 27.4% by weight hydrogen peroxide and 5.6% by weight peracetic acid and the solution was stored at ambient temperature.
Figure 14:
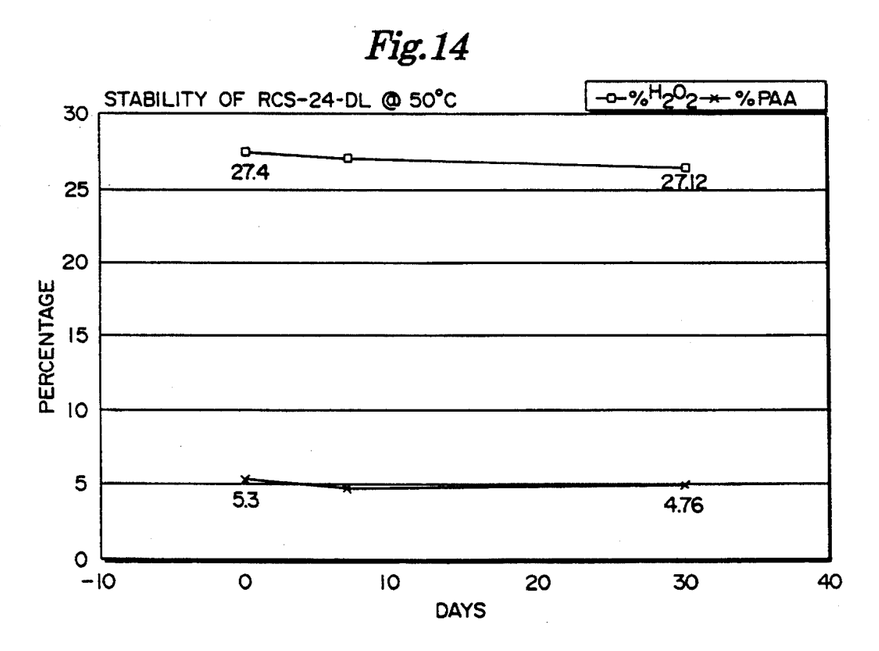
FIG. 14 is a chart of stability of the concentrated microbicide where the initial formulation contained 27.4% by weight hydrogen peroxide and 5.3% by weight peracetic acid and the solution was stored at 50° C.

The concentrate manufactured in accordance with the present invention is stored and shipped in amber colored plastic bottles that have been thoroughly precleaned with purified water to ensure no heavy metal contamination. Stability studies were run at ambient (22° C.), 35° C. and 50° C. to determine the stability of the concentrate over time at these temperatures. Data regarding the relative stability of $H_2O_2$ and HOOAc in the concentrate composition and the concentrate itself are shown in FIGS. 1–14. Acetic acid typically was not measured for stability since it is not one of the active ingredients of the concentrate composition; in other words, acetic acid has no microbicidal activity. As can be seen from FIGS. 1–15, the solutions were very stable.

In addition to stability studies, corrosivity studies were run on the concentrate compositions, the results of which may be seen by referring to Table IIA. Table IIB details the results of the corrosivity run on conventional art formulations while Table IIC details the results of corrosivity testing on the component parts of the conventional art formulation. Table IID details the results of corrosivity studies run on the use-dilution formulations of the conventional art and several of the preferred embodiments of the present invention.

Corrosivity studies were done using a variety of metal coupons. They included naval brass 464 and aluminum 5052. The coupons are commercially available from Metal Samples Company (Munford, Ala.)

Coupons were cleaned by the following methods to remove all foreign debris and to ensure accurate results. Brass coupons were placed on edge in a 50% by weight solution of HCl for two minutes at ambient temperature. Aluminum coupons were placed on edge in concentrated nitric acid for three minutes at ambient temperature. During all phases of the testing, coupons were handled by gloved laboratory personnel to insure that the coupons were not exposed to any foreign materials prior to placing them in the test solutions. All coupons are stamped with a number to aid in identification. All coupons were air dried under a ventilated hood and weighed prior to testing on a Mettler AE 100 analytical balance. The weight was recorded as the initial weight.

The exposure time of the coupons was 0.5 hours for brass and 5 hours for aluminum when testing the concentrate microbicide and 5 hours for brass and 1 week for aluminum when testing the use-dilution formulation of the microbicide. The coupons were tested in the test solutions indicated below at ambient temperature.

Solution volumes of 70 ml were dispensed into plastic disposable cups. The coupons were allowed to remain in solution for the times indicated above. After the time period had expired, the solution was discarded and the coupons were plated to dry, without rinsing, standing on edge in a ventilating hood. After drying for 30–60 minutes, the coupons were re-weighed. The difference between the initial weight and final weight (W) was used to calculated the corrosion rate as follows:

$$\text{Corrosion rate (mm/yr)} = \frac{(K \times W)}{(A \times T \times D)} \text{ where:}$$

K=a constant ($8.76 \times 10^{-4}$)

T=time of exposure in hours

A=area in $cm^{-2}$ ($28.7\ cm^{-2}$)

W=weight loss in grams (initial weight−final weight)*

*To correct for possible weight loss due to product removal, a "blank" coupon was weighed, cleaned by the procedure indicated above and weighed again.

D=density in $g/cm^{-3}$**

**Brass=$8.41\ g/cm^{-3}$

Aluminum 5052=$2.68\ g/cm^{-3}$

TABLE IIA

| Sam-ples | Titrations | | | Corrosion | |
|---|---|---|---|---|---|
| | $H_2O_2$ | PAA | HoAc | Brass | Aluminum |
| 1 | 38.8% | 4.54% | 2.88% | 19.9 mm/yr | 0.012 mm/yr |
| 2 | 34.8% | 4.23% | 3.27% | 33.3 mm/yr | .006 mm/yr |
| 3 | 27.6% | 5.0% | 6.1% | 52.02 mm/yr | .284 mm/yr |
| 4 | 27.4% | 5.4% | 6.2% | 58.91 mm/yr | .024 mm/yr |
| 5 | 27.3% | 5.5% | 5.7% | 52.07 mm/yr | .022 mm/yr |
| 6 | 27.55% | 5.03% | 6.06% | 52.02 mm/yr | .283 mm/yr |
| 7 | 27.4% | 5.4% | 6.21% | 58.91 mm/yr | .023 mm/yr |
| 8 | 27.34% | 5.51% | 5.68% | 58.07 mm/yr | .020 mm/yr |
| 9 | 27.2% | 5.72% | 6.67% | 57.56 mm/yr | .010 mm/yr |
| 10 | 27.2% | 5.70% | 6.82% | 54.53 mm/yr | .376 mm/yr |
| 11 | 27.0% | 5.62% | 6.66% | 49.96 mm/yr | .013 mm/yr |
| 12 | 27.0% | 4.00% | 5.71% | 82.10 mm/yr | .001 mm/yr |
| 13 | 26.5% | 4.14% | 6.50% | 93.70 mm/yr | .018 mm/yr |
| 14 | 22.5% | 4.19% | 7.84% | 95.62 mm/yr | 1.320 mm/yr |
| 15 | 22.5% | 3.91% | 8.1% | 93.25 mm/yr | .153 mm/yr |
| 16 | 22.5% | 3.86% | 8.1% | 93.20 mm/yr | .230 mm/yr |
| 17 | 19.6% | 2.68% | 8.62% | 45.3 mm/yr | .257 mm/yr |
| 18 | 16.9% | 1.66% | 6.26% | 43.4 mm/yr | .173 mm/yr |

TABLE IIB

| | Conventional Art Formulation | | | | | |
|---|---|---|---|---|---|---|
| | Titration | | | | | |
| | | | | Phosphonic Acid | Corrosivity | |
| Samples | $H_2O_2$ | PAA | HoAc | Stabilizer | Brass | Aluminum |
| 19 | 22.4% | 3.96% | 8.27% | 1.0% | 295.50 mm/yr | 121.63 mm/yr |
| 20 | 21.0% | 4.3% | 9.86% | 1.0% | 295.48 mm/yr | 121.65 mm/yr |

TABLE IIC

| Corrosivity of Component Parts | | |
|---|---|---|
| Samples | Brass | Aluminum |
| 1% stabilizer | .586 mm/yr | .367 mm/yr |
| 22.7% $H_2O_2$ | .528 mm/yr | .316 mm/yr |
| 10.2% HoAc | .160 mm/yr | .167 mm/yr |

TABLE IID

| Use-dilution Formulations* | | |
|---|---|---|
| Conventional Art | Brass | Aluminum |
| 3% Sample 19 | 23.63 mm/yr | 0.820 mm/yr |
| 3% Sample 20 | 23.84 mm/yr | 0.747 mm/yr |
| Present invention | | |
| Sample X [27% $H_2O_2$, 5.3% PAA, 5.5% Ac] | 12.77 mm/yr | 0.437 mm/yr |
| Sample Y [37% $H_2O_2$, 4.8% PAA, 2.2% Ac] | 5.39 mm/yr | 0.374 mm/yr |
| Sample Z [22% $H_2O_2$, 4.0% PAA, 7.0% Ac] | 14.63 mm/yr | 0.441 mm/yr |

TABLE IID-continued

Use-dilution Formulations*

| Conventional Art | Brass | Aluminum |
|---|---|---|

*All use-dilution samples were prepared using 3% of the concentrate formula diluted in a purified aqueous diluent.

In the present preferred form of the invention, the concentrate is shipped in a small quantity in an amber colored plastic bottle together with a gallon of purified deionized water. Before use, the concentrate of the preferred embodiment is diluted from about 20 to 40 times, more preferably from about 25 to 35 times, and most preferably from about 30 to 33 times with a purified aqueous diluent prepared as described below. This results in a use-dilution formulation of approximately 3.0% to 4.5% by volume of concentrate. Ordinary tap water is generally unsuitable as a diluent because of contaminants, such as divalent and trivalent ions, contained therein. If ordinary tap water is used to dilute the concentrate, the shelf life of the use-dilution formulation will likely be less than when the purified aqueous diluent is used and corrosivity will increase as the purity of the water decreases. The recommended shelf life of the use-dilution microbicide is seven days. Consequently, it may be used for several applications or reused several times during that period of time with no change in the stability or in the anticorrosive or sporicidal activity.

A purified aqueous diluent suitable for use in the concentrate and use-dilution formulation in accordance with the present invention is prepared in the following manner. Raw city water is passed through an activated carbon bed containing 10 cubic feet of carbon in a 24 in. diameter fiberglass tank with a 2 in. diameter super flow head and a 2 in. diameter distributor.

The water is then passed through softening beds well known in the art of water purification to remove calcium chloride and magnesium. Suitable softening beds are available from Eco water Systems (Woodbury, Minn.). The water is then passed through a one micron polypropylene cloth sediment filter having an efficiency rate of 93%. The cloth filter catches any particulate matter remaining in the water that has a size greater than $1_u$.

The water then flows through an eight inch diameter reverse osmosis membrane filter. The membrane filter is made from a spirally wound polyamide sheet membrane and is commercially available as Model No. BW-30 from Filmtec Co. (Edina, Minn.). The water effluent has less than 5 ppm dissolved solids.

After the water is treated by passing it through the reverse osmosis membrane, it is circulated through an ultraviolet disinfection unit. The unit employs dual wave lengths at 185 nm and 254 nm and is rated at 99%.9 bacterial reduction. A suitable commercially available unit is the Aquafine U.V. Water Sterilizer, CLS-4R (Aquafine Corp, Valencia, Calif.)

Post-UV light treatment, the water flows through an anion exchange resin bed and a cation exchange resin bed. The anion exchange resin bed is a strongly basic anion exchange resin based on a styrenedivinylbenzene copolymer matrix. Its exchange capacity is derived from the $N \cdot (CH_3)_2H_4OH$ (dimethylethanolamine) group. Anion exchange resin bed capable of purifying the aqueous diluent in accordance with the present invention may be purchased from Sybron Chemicals Inc (Birmingham, N.J.) under the trade name IONAC ASB-2. The cation exchange resin bed is a bead-form, standard crosslinked, polystyrene sulfonate cation exchange resin with a capacity of 1.4 mEq/ml for further demineralization. Treated water is stored in a 1000–5000 gallon tank. Resistivity is constantly measured and maintained at 17–17.5 mOhms.

Prior to using the above manufactured water in the concentrate mixtures or use-dilution formulations in accordance with the present invention, the water is tested for pyrogen, yeast, molds and bacteria by the following methods.

Pyrogen Testing. Five milliliters of sterile water is pipetted into a vials of endotoxin, commercially available as endotoxin from *E. coli* strain 055.B5 from Whittaker Bioproducts, Inc. (Walkersville, Md.). Five and two-tenths milliliters of sterile water is piperted into a vial of lysate, commercially available as Pyrogen T from Whittaker Bioproducts. One hundred lambda of the reconstituted lysate is then piperted into disposable conical tubes. The diluted lysate has a sensitivity of 0.06 endotoxin units.

Serial dilutions of the reconstituted endotoxin ranging from 500 picograms/ml to 12.5 picograms/ml are prepared. Positive controls are set up by pipetting 100 lambda of each of the above prepared dilutions of endotoxin into a conical tube containing the lysate. Tubes are mixed and placed in a 37° heating block for one hour±two minutes. Triplicate samples of 100 lambda each of ultra-pure deionized water as manufactured in accordance with the procedure disclosed herein are added to the lysate tubes and incubated at 37° C. for one hour. A gelled tube indicates the presence of endotoxin.

Yeast, Molds and Bacteria Testing

Water used in the manufacture of the concentrate microbicide and in the use-dilution formulation is tested for the presence of microbes using a filter membrane technique. Samples are collected aseptically in sterile 10 ml test tubes at the source. Five milliliters of sample is transfered into a 100 ml filter housing. A vacuum is applied to the filter housing to facilitate filtration. The lower housing is removed and the filtrate is decanted. The filter membrane is aseptically removed and placed in a tryprone glucose yeast agar plate (DiMed Corporation, St. Paul, Minn.) for measuring bacterial growth and potato dextrose agar plates (DiMed Corporation, St. Paul, Minn.) for measuring yeast and mold growth. The media plate is covered, inverted and incubated at 35° C. for two days for bacteria and at 22° C. for seven days for yeasts and molds. Results are reported as the number of colony forming units per five milliliters of sample size.

EXAMPLES

Example 1

All mixing drums and tanks were thoroughly cleaned using purified water. Sixty percent by weight of purified water was added to a cleaned mixing tank at ambient temperature. Bacterial testing and yeast and molds testing of the water used in manufacturing the concentrate was reported as 0 colony forming units per five milliliters of sample for both tests. An air driven drum pump was turned on to start recirculation of the batch. Fourteen percent by weight of acetic acid was added to the mixing tank containing the deionized water. After the acetic acid was added, the batch was covered and recirculated for one hour. Using an air driven drum pump, 26% by weight of hydrogen peroxide was added into the mixing tank and the cover replaced. The composition was recirculated for two hours after all chemicals were added. After two hours, the recirculating pump was stopped. The concentrate was dispensed into clean gallon drums for storage and equilibrated for 19 days. After 19 days from the production date, a sample was taken from the concentrate batch and the concentration was determined to be 22.5% $H_2O_2$, 3.96% peracetic acid, and 8.1% acetic acid.

Microbicidal Effectiveness

A 3.0% solution of the concentrate microbicide manufacture in Example 1 was tested for sporicidal activity according to the methods outlined in the Official Methods of Analysis of the Association of Official Analytical Chemists (K. Helrich 15th ed. 1990) (966.04 pp. 141–142), the text of which is hereby specifically incorporated by reference.

Briefly, cultures of two sporoformer organisms, *Bacillus subtilis* ATCC 19659 and *Clostridium sporogenes* ATCC 3584 were grown in the appropriate medium. Each organism was used to contaminate two types of carriers, namely, silk suture and porcelain penicylinders. The carriers were dried for a minimum of 24 hrs. under vacuum. Carriers were tested for acid resistance and viability. Five carriers were placed in test tubes containing 10 mL. of test solution, and exposed for 30 min. at 50° C. Following contact, carriers were neutralized in thioglycollate medium and incubated for 21 days at 37° C. If no growth was observed after 21 days, the test tubes were heat shocked for 20 minutes at 80° C. to activate any remaining spores and incubated for 72 hrs. at 37° C. For chemical sterilant claims, no survival of any organism/spore can be tolerated for qualification of the solution by the U.S. Environmental Protection Agency as a sterilant. The results of the sporicidal testing of the concentrate microbicide in accordance with the microbicide prepared in Example 1 are as follows:

| Lot | Org. | Carrier | Titer | Resistance | #Survivors/#Tested |
|---|---|---|---|---|---|
| 2M004 | Cl. sp. | Suture | $10^{-6}$ | 20 min. | 0/60 |
| 2M004 | Cl. sp. | Cylinder | $10^{-5}$ | 5 min. | 0/60 |
| 2M004 | B. sub. | suture | $10^{-4}$ | 20 min. | 0/60 |
| 2M004 | B. sub. | Cylinder | $10^{-4}$ | 2 min. | 0/60 |

The results of the AOAC procedure reference test shows that the microbicide of the invention, in addition to being stable, is effective as a sterilant.

Corrosivity of the solution of Example 1 was tested. The results appear as Sample 15 in Table IIA.

Example 2

All mixing drums and tanks were thoroughly cleaned using purified water. 23.3% by weight of purified water was added to a cleaned mixing tank at ambient temperature. Bacterial testing and yeast and molds testing of the water used in manufacturing the concentrate was reported as 0 colony forming units per five milliliters of sample for both tests. An air driven drum pump was turned on to start recirculation of the batch. 16.7% by weight of acetic acid was added to the mixing tank containing the purified water. After the acetic acid was added, the batch was covered and recirculated for one hour. Using an air driven drum pump, 40.0% by weight of hydrogen peroxide was added into the mixing tank and the cover replaced. The composition was recirculated for two hours after all chemicals were added. After two hours, the recirculating pump was stopped. The concentrate was dispensed into clean 55 gallon drums for storage. After 19 days from the production date, the batch was adjusted to a hydrogen peroxide level of 36.5% and a peracetic acid level of 4.5% by adding water and hydrogen peroxide. The solution was allowed to equilibrate for an additional 33 days. A sample was taken from the concentrate batch and the concentration was determined to be 36.65% hydrogen peroxide, 4.31% peracetic acid and 2.88%.

The results of the sporicidal testing of a 3% solution of the concentrate microbicide in accordance with the microbicide prepared in Example 2 are as follows:

| Lot | Org. | Carrier | Titer | Resistance | #Survivors/#Tested |
|---|---|---|---|---|---|
| 2008-2a | Cl. sp. | Suture | $10^{-6}$ | 20 min. | 0/60 |
| 2008-2a | Cl. sp. | Cylinder | $10^{-6}$ | 10 min. | 0/60 |
| 2008-2a | B. sub. | suture | $10^{-4}$ | 10 min. | 0/60 |
| 2008-2a | B. sub. | Cylinder | $10^{-4}$ | 2 min. | 0/60 |

The concentrate prepared in accordance with Example 2 was tested for corrosivity. The results are shown in Table IIA as Sample 2.

Example 3

Using the method set forth in Examples 1 and 2, 7.74% by weight purified water was added to 17.12% by weight $H_2O_2$ and 8.143% by weight HOAc. Bacterial testing and yeast and molds testing of the water used in manufacturing the concentrate was reported as 0 colony forming units per five milliliters of sample for both tests. After mixing for the specified time periods, the concentrate was allowed to stand for 19 days and a sample was taken to determine the content of $H_2O_2$ and HOOAc. The final concentration was determined to be 16.86% by weight $H_2O_2$, 1.66% peracetic acid and 6.26% acetic. The solution was found to have microbicidal activity as follows:

| Lot | Org. | Carrier | Titer | Resistance | #Survivors/#Tested |
|---|---|---|---|---|---|
| 2028-1 | Cl. sp. | Suture | $10^{-5}$ | 10 min. | 0/60 |
| 2028-1 | Cl. sp. | Cylinder | $10^{-6}$ | 10 min. | 0/60 |
| 2028-1 | B. sub. | suture | $10^{-4}$ | 10 min. | 0/60 |
| 2028-1 | B. sub. | Cylinder | $10^{-4}$ | 2 min. | 0/60 |

Corrosivity was tested and the results are detailed in Table IIA as Sample 18.

While the preceding compositions in accordance with the invention are the preferred form it is to be understood that concentrate formulations may be within the ranges given and still provide the advantages of the invention. Those skilled in the art may recognize other equivalents to the specific embodiments described herein which equivalents are intended to be encompassed by the appended claims.

We claim:

1. A stable, anticorrosive to surgical and dental metals concentrate consisting essentially of at equilibrium peracetic acid, acetic acid, hydrogen peroxide and an aqueous diluent, said concentrate characterized in having from about 0.001–200 ppm of stabilizers wherein said stabilizers are selected from the group consisting of phosphonic acids and sodium pyrophosphates, from about 5–10 ppm of divalent and trivalent ions wherein said divalent and trivalent ions are selected from the group consisting of iron, manganese, magnesium, nickel and cobalt and no added surfactants.

2. The concentrate in accordance with claim 1 wherein the concentration of said stabilizers are from about 0.001–100 ppm.

3. The concentrate is accordance with claim 1 wherein the concentration of said stabilizers is from about 0.001–10 ppm.

4. The concentrate of claim 1 wherein the equilibrium composition comprises:

| | |
|---|---|
| a) H$_2$O$_2$ | 16 to 38% by weight; |
| b) HOAc | 2.0 to 9.0% by weight; |
| c) HOOAc | 1.5 to 6.0% by weight; and |
| d) the balance is a purified aqueous diluent. | |

5. The concentrate in accordance with claim 4 wherein the concentration of said stabilizers is from about 0.001–100 ppm.

6. The concentrate in accordance with claim 4 wherein the concentration of said stabilizers is from about 0.001–10 ppm.

7. The concentrate in accordance with claim 1 wherein the equilibrium concentration comprises:

| | |
|---|---|
| a) H$_2$O$_2$ | 23 to 24% by weight; |
| b) HOAc | 9 to 10% by weight; |
| c) HOOAc | 4 to 6% by weight; and |
| d) the balance is a purified aqueous diluent. | |

8. The concentrate in accordance with claim 7 wherein the concentration of said stabilizers is from about 0.001–100 ppm.

9. The concentrate in accordance with claim 7 wherein the concentration of said stabilizers is from about 0.001–10 ppm.

10. A method of formulating a stable, anticorrosive to surgical and dental metals concentrate microbicide comprising the steps of:

a) blending hydrogen peroxide, acetic acid and a purified aqueous diluent to result in a solution which at equilibrium has from about 0.001–200 ppm stabilizers wherein said stabilizers are selected from the group consisting of phosphonic acids and sodium pyrophosphates, from about 5–10 ppm of divalent and trivalent ions wherein said divalent and trivalent ions are selected from the group consisting of iron, manganese, magnesium and cobalt and no added surfactants.

11. A method of formulating a stable, anticorrosive to surgical and dental metals concentrate microbicide comprising the steps of:

a) introducing from about 17% by weight to about 40% by weight hydrogen peroxide into a mixing drum, said hydrogen peroxide is characterized in having from about 0.001–200 ppm of stabilizers wherein said stabilizers are selected from the group consisting of phosphonic acids and sodium pyrophosphates;

b) blending thereinto from about 10% by weight to about 16% by weight acetic acid; and c) adding a purified aqueous diluent having from about 5–10 ppm of divalent and trivalent ions wherein said divalent and trivalent ions are selected from the group consisting of iron, manganese, magnesium, nickel and cobalt;

wherein the equilibrium concentration comprises:

i) from about 16–34% by weight hydrogen peroxide;

ii) from about 5–12% by weight acetic acid;

iii) from about 2.5–5.5% by weight peracetic acid; and iv) an aqueous diluent and wherein said equilibrium concentrate is characterized in having from about 0.001–200 ppm of stabilizers wherein said stabilizers are selected from the group consisting of phosphonic acids and sodium pyrophosphates, from about 5–10 ppm of divalent and trivalent ions wherein said divalent and trivalent ions are selected from the group consisting of iron, manganese, magnesium, nickel and cobalt and no added surfactants.

12. A stable, anticorrosive to surgical and dental metals use-dilution microbicide comprising:

a) a concentrate consisting essentially of at equilibrium peracetic acid, acetic acid, hydrogen peroxide and an aqueous diluent, said concentrate characterized in having from about 0.001– 200 ppm of stabilizers wherein said stabilizers are selected from the group consisting of phosphonic acids and sodium pyrophosphates, from about 5–10 ppm of divalent and trivalent ions wherein said divalent and trivalent ions are selected from the group consisting of iron, manganese, magnesium, nickel an cobalt and no added surfactants; and b) a purified aqueous diluent;

wherein said concentrate is diluted in said aqueous diluent from about 20 to 40 times.

* * * * *

UNITED STATES PATENT AND TRADEMARK OFFICE
CERTIFICATE OF CORRECTION

PATENT NO. : 5,508,046
DATED : April 16, 1996
INVENTOR(S) : Cosentino, et al.

It is certified that error appears in the above-indentified patent and that said Letters Patent is hereby corrected as shown below:

Column 2, line 4, delete "pm" and substitute --ppm-- therefor

Column 4, line 44, delete "$CH_3CO_2H+H_2O_2->CH_3CO_3H+H_2O$" and substitute --$CH_3CO_2H+H_2O_2<->CH_3CO_3H+H_2O$ -- therefor Column 5, line 29, delete "plated" and substitute --placed-- therefor Column 10, line 6, after "2.88%" insert --acetic acid--

Column 10, line 34, after "acetic" insert --acid--

Column 12, line 42, delete "an" and insert --and-- therefor

Signed and Sealed this

Tenth Day of September, 1996

Attest:

BRUCE LEHMAN

*Attesting Officer*          *Commissioner of Patents and Trademarks*